United States Patent [19]

Pengilly

[11] 4,192,862
[45] Mar. 11, 1980

[54] HAIRSPRAY CONTAINING A HAIRSPRAY RESIN AND A DRAG REDUCING AGENT

[75] Inventor: Roger W. Pengilly, Worcester Park, England

[73] Assignee: Lever Brothers Company, New York, N.Y.

[21] Appl. No.: 928,227

[22] Filed: Jul. 26, 1978

[30] Foreign Application Priority Data

Jul. 28, 1977 [GB] United Kingdom ............... 31780/77

[51] Int. Cl.² ............................................. A61K 7/11
[52] U.S. Cl. ................................... 424/47; 8/127.51; 252/305; 424/DIG. 1; 424/70; 424/71
[58] Field of Search ................... 424/DIG. 1, 47, 70, 424/71; 8/127.51; 252/305

[56] References Cited

U.S. PATENT DOCUMENTS

| | | | |
|---|---|---|---|
| 2,723,248 | 11/1955 | Wright | 424/47 |
| 3,142,622 | 7/1964 | Clapp | 424/47 |
| 3,210,251 | 10/1965 | Klug | 424/47 |
| 3,360,356 | 12/1967 | Vartiak | 71/65 |
| 3,479,427 | 11/1969 | Lieberman et al. | 424/47 |
| 3,715,428 | 2/1973 | Quasius et al. | 424/47 |
| 3,790,664 | 2/1974 | Krochock et al. | 424/47 |
| 3,876,760 | 4/1975 | Nersesian et al. | 424/70 |
| 3,914,403 | 10/1975 | Valan | 424/47 |
| 3,922,341 | 11/1975 | Abegg et al. | 424/47 |
| 3,928,558 | 12/1975 | Cheesman et al. | 424/47 |
| 3,958,581 | 5/1976 | Abegg et al. | 424/47 X |
| 3,959,463 | 5/1976 | Nersesian et al. | 424/70 |
| 3,984,536 | 10/1976 | Viout et al. | 424/47 |

FOREIGN PATENT DOCUMENTS

| | | |
|---|---|---|
| 46-27479 | 10/1971 | Japan . |
| 747806 | 4/1956 | United Kingdom . |
| 1161642 | 8/1969 | United Kingdom . |

*Primary Examiner*—Bernard Helfin
*Assistant Examiner*—Vera C. Clarke

[57] ABSTRACT

The invention relates to a hairspray product having improved hair-holding properties. The hairspray composition comprises, as is usual, a solution of a hairspray resin in a suitable solvent, but to improve the holding power there is also included a minor amount of a drag reducing agent which is soluble in the solvent for the hairspray resin. The drag reducing agent is present in an amount such that the weight ratio of the hairspray resin to the drag reducing agent is 10,000 to 2:1. The drag reducing agent amounts to less than 0.3% by weight of the composition.

13 Claims, No Drawings

HAIRSPRAY CONTAINING A HAIRSPRAY RESIN AND A DRAG REDUCING AGENT

This invention relates to hairsprays, sometimes called hair lacquers.

Hairsprays are products containing a film-forming resin which when applied to the hair help to hold the hair in place. The film-forming resin can be sprayed onto the hair utilising different types of dispenser. Most hairspray products utilise an aerosol container, from which the hairspray composition is discharged by a propellant, but becoming more common as dispensers at the present time are pump spray applicators, which utilise a mechanical pump for the discharge of the composition comprising the film-forming resin. Hairspray compositions can also be applied to the hair from a so-called squeeze pack, the pressure generated by squeezing the pack being utilised for the discharge of the composition through the spray orifice. The composition sprayed onto the hair comprises a solution of the hairspray resin in a suitable solvent, usually an alcoholic or aqueous alcoholic solvent.

This invention is concerned with improving the holding power of a hairspray.

We have discovered that an unexpected increase in the holding power of a hairspray can be obtained simply by including in the hairspray composition a small amount of a drag reducing agent.

According to the invention there is provided a hairspray product consisting of a hairspray composition within a container for spraying the composition onto the hair, wherein the hairspray composition comprises 0.4 to 7.5% by weight of the composition of a hairspray resin, and a solvent for the hairspray resin, the composition also comprising a drag reducing agent dissolved in the solvent whereby the holding power of the hairspray composition is improved, the weight ratio of the hairspray resin to the drag reducing agent being 10,000 to 2:1 and the amount of the drag reducing agent being less than 0.3% by weight of the hairspray composition.

By the invention the holding power of the applied hairspray resin can be very considerably enhanced and to a degree far exceeding any benefit that could be predicted. Indeed, the amounts of added drag reducing agent which are effective to improve the holding power of a hairspray, as demonstrated hereinafter, are so small that no measurable improvement at all in hold would have been expected.

It is known that the addition of even minute amounts of certain high molecular weight polymers can be used to reduce the frictional drag resistance forces between a liquid in turbulent flow and a solid surface over which the liquid flows (see the papers "Drag Reduction Characteristics of Solutions of Macromolecules in Turbulent Pipe Flow" by J. G. Savins published in Society of Petroleum Engineers Journal, September 1964, pages 203 to 214; "Turbulence Damping and Drag Reduction Produced by Certain Additives in Water" by G. E. Gadd published in Nature, May 1, 1965; pages 463 to 467; and "Reduction of Friction in Oil Pipelines by Polymer Additives" by A. Ram, E. Finkelstein and C. Elata published in I and EC Process Design and Development, Volume 6, No. 3, July 1967, pages 309 to 313). An effect of the addition of a drag reducing polymer is to increase the volumetric flow of liquid through a pipe. We utilise this phenomenon to define the drag reducing agent used in a hairspray of this invention. The drag reducing agent should have a drag reduction efficiency of at least 2% determined as described.

A polymeric material is tested for its drag reduction potential by determining its effect on the flow rate of a solvent for the hairspray resin (in which it is required to be soluble) by feeding a solution of the material, in a concentration specified below, at room temperature (about 20° C.) and pressure of 15 psig (1 kg cm$^{-2}$ guage) to a capillary tube of length 32 cms and capillary diameter 1.5 mm. The drag reduction efficiency of the material, expressed as a percentage, is given by the expression $$\left( \frac{f_{solution} - f_{solvent}}{f_{solvent}} \right) \times 100$$

where $f_{solvent}$ is the discharge rate of the solvent and $f_{solution}$ is the discharge rate of the solution of the polymer in the solvent. Drag reduction efficiencies referred to herein are determined using solutions of concentration 0.01% or 0.10% w/w. A material is to be understood herein as having a drag reduction efficiency of at least 2% if its drag reduction efficiency at a solution concentration of 0.01% and/or 0.10% w/w is at least 2%. Experiments have shown that drag reduction efficiency is substantially independent of the nature of the hairspray solvent. Consequently, it is usually convenient to test materials for their drag reducing efficiency in either water or, if not soluble therein, in methylene chloride. If a material has a drag reduction efficiency of at least 2% in one of these solvents it will be readily possible to formulate a solvent system for a hairspray resin and the drag reducing agent based on one or more of the conventional hairspray solvents, particularly lower aliphatic alcohols, methylene chloride and mixtures thereof with or without water. In carrying out the present invention it is preferred to employ drag reducing agents which have a drag reduction efficiency of at least 10%.

A particularly effective group of materials for enhancing the holding power of hairspray resins are certain polyoxyethylenes. These non-ionic polymeric materials are soluble in water and mixtures of water and organic hairspray solvents and are effective in enhancing the holding power of a hairspray at very low levels, particularly in the case of those polyoxyethylenes having an average molecular weight exceeding one million which are effective even at levels of less than 50 parts per million of the hairspray composition. Water soluble polymers of ethylene oxide are commercially available from Union Carbide Corporation under the trade name POlYOX Water Soluble Resins (POLYOX is a trade mark).

The members of the commercially available Polyox range of polyoxyethylene resins that are drag reducing agents are indicated below, the information regarding viscosity and approximate weight average molecular weights being taken from trade literature supplied by the Union Carbide Corporation.

Viscosity Data (at 25° C.) of an aqueous solution of the polyoxyethylene resin

| Polyox Grade | Solution Concentration | Viscosity (cps) | Brookfield Spindle No./ Speed | Average Molecular Weight |
| --- | --- | --- | --- | --- |
| Polyox Coagulant | 1% | 5000–8000 | 2/2 RPM | $5 \times 10^6$ |
| Polyox 301 | 1% | 1500–3500 | 1/2 RPM | $4 \times 10^6$ |
| Polyox 205 | 5% | 4100–8000 | 2/2 RPM | $6 \times 10^5$ |
| Polyox 3000 | 5% | 2250–3350 | 1/1 RPM | $4 \times 10^5$ |
| Polyox 750 | 5% | 550–900 | 1/10 RPM | $3 \times 10^5$ |
| Polyox 80 | 5% | 55–95 | 1/50 RPM | $2 \times 10^5$ |

Typical values for the drag reduction efficiency of these polyoxyethylene resins are given below. Water is a suitable solvent for the determination of drag reduction efficiency.

| Polyoxyethylene | Drag Reduction Efficiency (%) | |
| --- | --- | --- |
| | 0.01% w/w concentration | 0.10% w/w concentration |
| Polyox Coagulant | 15 | —* |
| Polyox 301 | 25 | —* |
| Polyox 305 | 22 | —* |
| Polyox 3000 | 23 | 13 |
| Polyox 750 | 10 | 20 |
| Polyox 80 | less than 2 | 5 |

*Negative values were obtained

The polyoxyethylene designated Polyox 10 (average molecular weight about $1 \times 10^5$) is not a drag reducing agent. At both 0.01% and 0.10% concentrations in water it was not shown to exhibit any drag reducing properties. With regard to the obtaining of negative values for the drag reduction efficiency in certain cases as indicated above, it should be explained that these polymers tend to increase the viscosity of solvents and this will of course tend to reduce the rate of flow of the solvent through the capillary tube. The consequence is that above a certain level of addition, depending on the molecular weight of the polyoxyethylene, the net effect of the additive is to reduce the rate of flow of the solvent. However, this effect appears to be of no significance as far as the present invention is concerned. It is only important that the polymer should have a drag reduction efficiency of at least 2% as determined above.

An especially useful group of hair hold enhancing agents are certain hydroxypropylcellulose polymers which are soluble in the polar organic solvents, e.g. lower aliphatic alcohols, usually used as solvents for hairspray resins. These non-ionic polymers, which are also soluble in water, are therefore particularly useful additives for a wide range of hairspray products in order to improve holding power. Hydroxypropylcelluloses are commercially available from Hercules Incorporated under the trade name KLUCEL. These hydroxypropylcelluloses have a degree of substitution (MS) within the range 2.5 to 10, the MS being the average number of hydroxypropyl groups per anhydroglucose unit.

The members of the commercially available Klucel range of hydroxypropylcellulose resins that are drag reducing agents are indicated below, the information regarding viscosity and average molecular weight being taken from trade literature supplied by Hercules Incorporated.

Viscosity data (at 25° C.) of an aqueous solution of the hydroxypropyl cellulose

| Klucel Grade | Solution Concentration | Viscosity (cps) | Brookfield Spindle No./ Speed | Average Molecular Weight |
| --- | --- | --- | --- | --- |
| Klucel H and HF* | 1% | 1500–2500 | 3/30 RPM | $1 \times 10^6$ |
| Klucel M and MF | 2% | 4000–6500 | 4/60 RPM | $7 \times 10^5$ |
| Klucel G and GF | 2% | 150–400 | 2/60 RPM | $3 \times 10^5$ |
| Klucel J and JF | 5% | 150–400 | 2/60 RPM | $2 \times 10^5$ |

*"F" grades are grades particularly suitable for use in food, pharmaceuticals and cosmetics.

Typical values for the drag reduction efficiency of these hydroxypropyl celluloses are given below. Water is a convenient solvent for the determination of drag reduction efficiency.

| Hydroxypropyl Cellulose | Drag Reduction Efficiency (%) | |
| --- | --- | --- |
| | 0.01% w/w Concentration | 0.10% w/w Concentration |
| Klucel H (HF) | 9 | 20 |
| Klucel M (MF) | 6 | 12 |
| Klucel G (GF) | 3 | 8 |
| Klucel J (JF) | 2 | 5 |

The lower molecular grade L (LF) having a viscosity in 5% solution of 75–150 cps (Brookfield Spindle No. 1, 30 RPM), and average molecular weight about $1 \times 10^5$, and the E (EF) grade having a viscosity in 10% aqueous solution of 300–700 cps (Brookfield Spindle No. 2, 60 RPM) and average molecular weight about $0.6 \times 10^5$ are not drag reducing agents. At both 0.01% and 0.10% concentration in water neither of these hydroxypropyl celluloses was shown to exhibit any drag reducing properties.

Further useful drag reducing agents for enhancing the holding power of a hairspray resin are polyacrylic elastomers, for example the poly(ethyl acrylate) elastomer commercially available from the B. F. Goodrich Chemical Company under the trade name "Hycar 4021-45". This non-ionic material consists essentially of polymerised ethyl acrylate although it comprises 1 to 5% of a compound providing reactive cure-sites, and believed to be 2-chloroethyl vinyl ether, since the polymer is intended for use as a vulcanisable rubber. Poly(ethyl acrylate) is not soluble in water or alcoholic solvents but is soluble in methylene chloride and therefore can be used in hairsprays containing methylene chloride as a solvet. It had a drag reduction efficiency of 12% at 0.01% concentration and a drag reduction efficiency of 30% at 0.10% concentration.

A further type of polymer shown to be effective as a drag reducing agent is a very high molecular weight cationic cellulosic polymer having the structural formula:

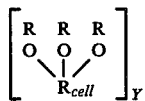

wherein $R_{cell}$ represents the residue of an anhydroglucose unit, wherein each R individually represents a substituent group of the following general formula:

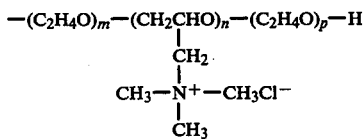

where m is a whole number of from 0 to 10, n is a whole number of from 0 to 3, and p is a whole number of from 0 to 10, and Y is an integer such that the polymer has a viscosity of from 1,000 to 2,500 centipoises in a 1% aqueous solution at 25° C. (Brookfield viscometer LVF, 30 rpm, spindle No. 3). The average values per anhydroglucose unit are: n from 0.35 to 0.45 and the sum of m+p is from 1 to 2. A suitable cationic cellulosic resin is that available commercially from the Union Carbide Corporation under the trade name "Polymer JR 30M". This polymer is less useful than the other drag-reducing agents referred to above as it requires the use of relatively large amounts of water to be present in the composition to act as solvent since it is not soluble in ethanol or methylene chloride. Lower viscosity grades of these cationic cellulosic polymers such as the grades available under the trade names Polymer JR 125 (viscosity at 25° C. in 2% solution of 75–175 centipoises, Brookfield Spindle No. 1, 30 rpm) and Polymer JR 400 (viscosity at 25° C. in 2% solution of 300–500 centipoises, Brookfield Spindle No. 2, 30 rpm) are not drag reducing agents. Neither of these lower molecular weight cationic cellulosic polymers was shown to exhibit any drag reducing properties at concentrations of 0.01% and 0.10%.

Preferred drag reducing agents are those which are soluble in either ethanol or methylene chloride. It is also preferred to employ drag reducing agents that are solid at normal temperature (25° C.).

A wide variety of hairspray resins have been used in commercially sold hairspray products. These include polyvinylpyrrolidone; copolymers of from 92.5 to 87.5% vinyl acetate and from 7.5 to 12.5% crotonic acid as described in U.S. Pat. No. 2,996,471, e.g. National Starch Resyn 28-1310; terpolymers of from 7 to 89% vinyl acetate, 6 to 13% crotonic acid and from 5 to 80% of a vinyl ester of an alpha-branched saturated aliphatic monocarboxylic acid having a minimum of five carbon atoms in the carboxylic moiety, said acid having the formula $R_3C(R_1)(R_2)COOH$ where $R_1$ and $R_2$ are alkyl radicals and $R_3$ is selected from hydrogen, alkyl, alkaryl, aralkyl and aryl radicals, such terpolymers being described in British specification No. 1,169,862 and U.S. Pat. No. 3,810,977, a commercially available terpolymer of this type being that sold under the name National Starch Resyn 28-2930; terpolymers of vinyl acetate; crotonic acid and either a vinyl ester of the formula $R\text{---}COOCH\text{=}CH_2$, wherein R represents a linear or branched chain hydrocarbon radical containing 10 to 22 carbon atoms, or an alkyl or methallyl ester of the formula $R'\text{-}COOCH_2\text{-}C(R'')\text{=}CH_2$ wherein R' represents a linear or branched chain hydrocarbon radical containing 10 to 22 carbon atoms, and R" represents a hydrogen atom or a methyl radical, such terpolymers being described in British specification No 1,153,544 and U.S. Pat. No. 3,579,629; copolymers of from 20 to 60% of N-vinyl pyrrolidone and from 40 to 80% of vinyl acetate such as those described in U.S. Pat. No. 3,171,784, and which copolymers are commercially available under the designations Luviskol 37E and Luviskol 28I; copolymers of maleic anhydride (1 mole) and an olefin (1 mole) containing 2 to 4 carbon atoms, particularly ethylene, said copolymer having a molecular weight of about 25,000 to 70,000, preferably being esterified to the extent of 50 to 70% with a saturated aliphatic alcohol containing from 1 to 4 carbon atoms, such as are described in U.S. Pat. No. 2,957,838; amphoteric acrylic resins as described in U.S. Pat. No. 3,726,288, such as the acrylamide/acrylate/butylaminoethyl methacrylate terpolymer containing carboxy groups available commercially under the trade name Amphomer; and copolymers of methyl vinyl ether and maleic anhydride (molar ratio about 1:1) and such copolymers esterified with a saturated aliphatic alcohol containing from 1 to 4 carbon atoms, an example thereof being the resin available commercially under the trade name Gantrez ES425. However, those skilled in the art will appreciate that other resins are suitable for use in hairsprays, see for example the section entitled "Hair Lacquers or Hair Sprays" commencing on page 352 of Volume 2 of "Cosmetics Science and Technology", Second Edition, edited by M S Balsam and Edward Sagarin (1972), and the section entitled "Hair Spray Resins" commencing on page 411 of "Harry's Cosmeticology", 1973.

Those copolymers which contain acidic groups and are water-insoluble are usually used in their neutralised water-soluble form. Suitable neutralising agents which may be included in the hairspray composition are amines, especially aminoalcohols, preferably 2-amino-2-methyl-1,3-propanediol and 2-amino-2-methyl-1-propanol. Other suitable neutralising agents are also given in U.S. Pat. No. 2,996,471.

Carrier liquids or solvents for the hairspray resin which are commonly used in formulating hairspray compositions are ethanol, isopropanol, methylene chloride, 2-methoxyethanol and 2-ethoxyethanol, and mixtures thereof with water. The carrier liquid may comprise more than one of these organic solvents. It is required, of course, that the carrier liquid for the resin should also be a solvent for the drag reducing agent. The solvent will usually amount to from about 5% to about 99.5% by weight of the composition. In aerosol products the solvent will be from about 5% to about 95% by weight, usually from about 10% to about 90% by weight.

In the case of aerosol hairspray products the composition within the container will also include a propellant such as a liquefied gas propellant or a compressed gas propellant. Well known liquefied gas propellants are the halogenated hydrocarbons and the liquefiable hydrocarbons. Commonly used liquefied gas propellants are trichlorofluoromethane (propellant 11), dichlorodifluoromethane (propellant 12), butane and propane, and mixtures thereof. Other suitable propellants are referred to in U.S. Pat. Nos. 3,026,250, 3,145,147 and 2,957,838, and more generally in the section entitled "Propellants" commencing on page 443 of Volume 2 of "Cosmetics Science and Technology" referred to previously. Liquefied gas propellants are generally used in amounts within the range 10 to 90% by weight of the hairspray composition. Examples of compressed gas propellants are carbon dioxide, nitrogen and nitrous oxide. These propellants are usually used in an amount of from about 1% to about 10% by weight of the total hairspray composition. Liquefied gas propellant may or may not be miscible with the solvent for the hairspray resin and drag reducing agent.

The use of pump spray applicators for dispensing a wide variety of compositions is now very well known and their use for dispensing hairspray compositions is referred to in Soap, Perfumery and Cosmetics (SPC), March 1977, pages 89–93. A number of mechanical pumps are described in Modern Packaging, October 1975, pages 15–20.

The amount of the drag reducing agent which is incorporated in the hairspray composition to increase the holding power of the hairspray resin is relatively small. The amount required will depend both on the molecular weight and on the chemical type of the drag reducing agent in so far as these affect drag reduction efficiency. Improvements in holding power have been obtained in certain cases with amounts of the drag reducing agent as small as 0.001% by weight of the composition or even less. As a general rule, for aerosol products somewhat higher amounts are desirable as the proportion of propellant in the composition is increased. Generally the more efficient the drag reducing agent, the smaller the amount required to be incorporated in the hairspray composition to improve the holding power. For this reason, within the series of, for example, the polyoxyethylene resins or the hydroxypropyl cellulose resins, the use of the higher molecular weight members is preferred. The polyoxyethylene and hydroxypropyl cellulose polymers of molecular weight of at least 400,000 and 500,000, respectively, are particularly preferred for this reason. There is, however, a practical limit to the amount that any given drag reducing agent can be included in a hairspray composition. Excessive amounts deleteriously affect the spray properties so that the product would no longer be regarded as acceptable. Excess amounts of drag reducing polymer can lead to the production of a spray with a very small cone angle, (or even to the production of a jet or stream rather than a spray) or to an unacceptably coarse spray where the droplets are too large. For these reasons the amount of the drag reducing agent should be less than 0.3% by weight of the hairspray composition. It is preferred that the drag reducing agent should not exceed 0.2% by weight of the composition. As a general rule the more effective the polymer as a drag reducing agent the smaller the amount that can be included in a hairspray. However, suitable amounts of drag reducing agent can readily be determined by those skilled in the art.

The holding power of a hairspray product obviously also depends on the amount of the hairspray resin present in it. It is usual in conventional products to include at least about 1% by weight of hairspray resin in order for the product to impart a satisfactory hold to the hair. Amounts in the range about 1 to 3% by weight are therefore quite normal in commercial products although if a product is required to have a higher than normal holding power the amount of resin can be correspondingly increased. An important practical consequence of our discovery that the inclusion of a drag reducing agent in a hairspray product can improve the holding power of the product is that it enables one to substantially reduce the level of hairspray resin without loss of product efficacy. Therefore in the hairspray product of the invention the amount of the hairspray resin can be as little as about 0.4% by weight of the composition while still retaining good hold properties. The upper limit of resin is not critical. The amount of hairspray resin will generally be in the range 0.4 to 7.5%, more usually 0.4 to 5%, by weight of the composition.

It will be evident from the above discussion of the deleterious effect on spray properties of the inclusion of high levels of drag reducing agent in hairspray products that the hairspray resins used in commercial products are themselves not drag reducing agents. The hairspray polymers commonly used are of relatively low molecular weight compared to the drag reducing agents referred to above.

A surprising feature of the present invention is that the drag reducing agent gives a substantial improvement in the holding power of the hairspray even though added in a minor amount compared to the amount of hairspray resin present. In the hairspray products of this invention the weight ratio of the hairspray resin to the added drag reducing agent is preferably at least 5:1. When a drag reducing agent of especially high effectiveness is used the amount which may be added can be very small indeed and could be as little as one ten-thousandth part of the resin, particularly when higher levels of hairspray resin are employed. The weight ratio of hairspray resin to drag reducing agent will normally be in the range 5000 to 5:1.

Together with the hairspray resin, solvent, drag reducing agent and, optionally, propellant, the hairspray composition may also include various other ingredients well known in the art. Examples of such other ingredients are perfume; alcohol denaturants, for example benzyl diethyl 2,6-xylyl carbamoyl methyl ammonium benzoate and sucrose octa-acetate; conditioning agents such as lanolin derivatives; and plasticisers such as silicone oils having a viscosity of 10 centistokes at 25° C.

The inclusion of the drag reducing agent can also result in a substantial reduction in the respirable fraction of the spray. Some of the particles of the aerosol cloud produced on spraying a hairspray composition may be inhaled by the user or by other persons in the vicinity. The inclusion of the drag reducing agent can reduce the amount of hairspray inhaled into the lungs. The proportion of the product discharged which is capable of reaching and being deposited in the lung is called herein the "respirable fraction" of the product.

The invention will now be illustrated by reference to Experiment Nos. 1 to 23. Percentages are by weight unless otherwise specified.

In Experiments 1 to 15 two methods of comparing the hair holding power of hairspray compositions are referred to and these methods will first be described.

The Switch Test Method

In this test method trained assessors compared in a subjective assessment method the holding power of various hairsprays applied to hair switches. The assessors selected for both test methods were those whose assessment of the holding power and other attributes of hairspray products was in good agreement with findings from large scale consumer tests.

In this test hair switches of good quality untreated hair about 20–25 cms long, 2 cms wide and weighing about 8 to 10 g were used. To prepare the switches for the test, they were shampooed, dried, suspended and then brushed through. Between successive applications of hairspray, the switches were brushed out until judged to be free of any bonding between the hairs.

The switches were divided into groups, the number of switches in each group corresponding to the number of hairsprays being compared. The number of groups of switches varied from 3 to 5.

Each product was applied to the same switch in a group throughout the test, there being a minimum of three applications of the product to a switch. After each application the holding power of the spray applied to each switch was assessed by one of the assessors. After each application, e.g. the first application, each switch in a group was assessed by the same assessor but each group was assessed by a different assessor. However, for a given group the assessor was usually different for the different applications of the test products. The number of applications varied from 3 to 5.

Within a given test, the distance for spraying and the time of spraying were the same for each product. They differed between tests, however, according to the particular products being tested.

After each application of a spray the switches were left to dry and then the assessor ranked the effect of the applied spray on a 10 point scale, 1 representing best hold and 10 no hold. The scores for each product were then averaged to obtain a hold value for a given product. Therefore if there were 3 groups of switches and 3 applications of test spray then the hold value was an average of 9 scores; if there are 5 groups and 5 applications are made then the hold value was an average of 25 scores. On repeating tests it was found that the hold values varied over about 0.5 unit.

Comparison between hold values for products obtained in different tests cannot be made as the spraying distance and spray times were not necessarily the same for the different tests and more importantly, a number of different spray valves and actuator combinations were used for spraying the test products, although of course within a given test these were maintained the same.

The Salon Test Method

This method of testing hairsprays is what is known as a half-head which is carried out in a hair salon. After shampooing and setting the hair, one side of a panellist's head was sprayed with a control product and the other side with a test product, a shield being placed centrally across the top of the head to confine a spray to one side of the head. After allowing the spray to dry (10 to 30 minutes) the hair hold was assessed comparatively by blowing each side of the head separately with a hand hair dryer (but without heat) and noting which side is disturbed least during blowing and least dissarranged after blowing has been stopped.

On the second day the panellist's hair is brushed out and styled whereafter the control and test products are applied and assessed as before. The procedure on the second day is then repeated on the third, fourth and fifth days.

The results of the test are then analysed statistically. The number of panellists in a test varied from 18 to 24.

The respirable fraction data given in Experiments 16 to 23 were determined using an Hexhlet elutriator (Brit. J. Industr. Med., 1954, 11, 284) which separates particles according to their falling velocities in the air. The aerosol is drawn at a controlled horizontal velocity through a parallel plate elutriator; the vertical spacing of the plates is such that particles settling on them during the transit of the aerosol through the elutriator correspond to those which would separate aerodynamically in the upper respiratory tract of man. Thus the particles passing through the elutriator and collected on a filter represent those which would penetrate to the human lungs. The upper aerodynamic size limit for respirable particles collected in the Hexhlet is about 7 microns.

The procedure was as follows. A glass fibre filter, dried and weighed, was loaded into the Hexhlet sampler and the pack to be treated was weighed. The vacuum was adjusted so that the guage on the Hexhlet showed about 300 mm Hg. After thoroughly shaking the pack, the product was sprayed into a cabinet fitted to the front of the Hexhlet sampler. In the case of aerosols, each spray was of 2 second duration, the sprays being repeated with shaking every 20 seconds for a total of 20 sprays. In the case of pump sprays the procedure was to give 10 sprays in rapid succession at the commencement of every 20 second period for a total of 200 sprays. Sampling was continued for 5 minutes after the last spray. The pack was re-weighed to give the weight of the product discharged. The weight collected is expressed in milligrams per 100 g of product discharged. This weight (referred to herein as the RF0 value) is a measure of the respirable material in an aerosol cloud. In some cases the filter was heated at 50° C. for 24 hours and then re-weighed. In this way the weight of non-volatiles collected was determined and this weight was also expressed in milligrams per 100 g of product discharged. This weight (referred to herein as the RF1 value) is a measure of the respirable non-volatiles in an aerosol cloud. The use of the Hexhlet in determining respirable fractions is also described in Aerosol Age, Volume 21, No 11, November 1976, pages 20 to 25.

The measurement of respirable fraction was carried out at a relative humidity of 50% and a temperature of 20° C. Each value of the pair of RF0 values (i.e., the RF0 values for the test and control products), and similarly RF1 values where determined, from which the percentage reduction in the RF0 or $RF_1$ value was calculated was the average of six measurements (two determinations on each of three packs). The actual numerical values of RF0 and RF1 are dependent on the specific value/actuator combination employed and therefore in a comparative test the same combination was used.

The composition of various control hairsprays employed in the experiments are given in the following table.

| CONTROL FORMULATIONS | | | | | |
|---|---|---|---|---|---|
| Ingredient No. | Description | I | II | III | IV |
| 1 | Resyn 28-2930 | 1.20 | — | — | 1.35 |
| 2 | Resyn 28-1310 | — | 1.80 | — | — |
| 3 | Luviskol 37E | — | — | 2.00 | — |
| 4 | PVP K30 | — | — | — | — |
| 5 | Gantrez ES 425 | — | — | — | — |
| 6 | Amphomer | — | — | — | — |
| 7 | 2-Amino-2-methyl-1-propanol | 0.12 | 0.16 | — | 0.13 |
| 8 | Silicone glycol | 0.04 | — | — | 0.04 |
| 9 | Sucrose octaacetate | — | 0.06 | — | — |
| 10 | Bitrex | — | 0.04 | — | — |
| 11 | Lanolin derivative (Lanexol) | — | 0.04 | — | — |
| 12 | Perfume | 0.06 | 0.13 | 0.08 | 0.12 |
| 13 | Absolute alcohol | 8.58 | — | 7.92 | 14.36* |
| 14 | Industrial Methylated Spirit | — | 37.77* | — | — |
| 15 | Methylene chloride | 27.00* | — | 24.00* | — |
| 16 | Water | — | — | — | — |
| 17 | Propellant 11 | 37.80 | 39.00 | 39.60 | 55.50 |
| 18 | Propellant 12 | 25.20 | 21.00 | 26.40 | 18.50 |
| 19 | CAP 40 | — | — | — | 10.00 |

| Ingredient No. | V | VI | VII | VIII |
|---|---|---|---|---|
| 1 | 1.40 | — | — | 1.22 |
| 2 | — | — | — | — |
| 3 | — | — | — | — |
| 4 | — | 1.00 | — | — |
| 5 | — | — | 3.00 | — |
| 6 | — | — | — | — |
| 7 | 0.12 | — | 0.64 | 0.12 |
| 8 | — | — | — | — |
| 9 | — | — | — | — |
| 10 | — | — | — | — |
| 11 | — | — | — | — |
| 12 | 0.14 | — | 0.15 | 0.08 |
| 13 | 48.34* | 29.00* | — | 4.95 |
| 14 | — | — | 36.21* | — |
| 15 | — | — | — | 20.63* |
| 16 | — | — | — | — |
| 17 | 25.00 | 21.00 | 39.00 | 43.80 |
| 18 | 25.00 | 49.00 | 21.00 | 29.20 |
| 19 | — | — | — | — |

| Ingredient No. | IX | X | XI | XII | XIII |
|---|---|---|---|---|---|
| 1 | 1.20 | — | 1.35 | 3.00 | 2.00 |
| 2 | — | — | — | — | — |
| 3 | — | — | — | — | — |
| 4 | — | — | — | — | — |
| 5 | — | — | — | — | — |
| 6 | — | 1.50 | — | — | — |
| 7 | 0.12 | 0.31 | 0.13 | 0.30 | 0.19 |
| 8 | 0.04 | — | 0.05 | — | — |
| 9 | — | — | — | — | — |
| 10 | — | — | 0.10 | — | — |
| 11 | — | — | — | — | — |
| 12 | — | 0.15 | 0.06 | — | — |
| 13 | 5.00 | — | 13.31* | 4.95 | 44.81* |
| 14 | — | 38.04* | — | — | — |
| 15 | 35.00* | — | — | 18.75* | — |
| 16 | — | — | — | — | 28.00 |
| 17 | 25.23 | 39.00 | 51.00 | 43.80 | — |
| 18 | 8.41 | 21.00 | 34.00 | 29.20 | — |
| 19 | 25.00 | — | — | — | 25.00 |

The materials used in the above control formulations and designated by trade names are described below.

Resyn 28-2930 is a terpolymer of vinyl acetate (75%), crotonic acid (10%) and vinyl versatate (15%) available from National Starch and Chemical Corporation. It has a number average molecular weight of about 22,500.

Resyn 28-1310 is a copolymer of vinyl acetate (90%) and crotonic acid (10%) also available from National Starch and Chemical Corporation. It has a number average molecular weight of about 25,000.

Luviskol 37 E is a 50% w/w solution in ethanol of a copolymer of vinyl pyrrolidone (30%) and vinyl acetate (70%) available from GAF Corporation.

PVP K-30 is a vinyl pyrrolidone polymer having a molecular weight of 40,000, also available from GAF Corporation.

Gantrez ES 425 is a 50% w/w solution in ethanol of a copolymer of methyl vinyl ether and maleic anhydride butyl monoester, also available from GAF Corporation.

Amphomer is an amphoteric acrylamide/acrylate/butylaminoethyl methacrylate terpolymer containing unneutralised carboxy groups available from National Starch and Chemical Corporation.

Bitrex is a 0.256% w/v solution in water of benzyl diethyl 2,6-xylyl carbamoyl methyl ammonium benzoate.

CAP 40 is a hydrocarbon consisting mainly of a mixture of propane and butanes having a vapour pressure of about 3.2 bars at 25° C. available from Calor Gas Ltd.

The silicone glycol was a polydimethylsiloxanepolyoxyethylene block copolymer as described in U.S. Pat. No. 3,928,558.

The following description includes results on the above control formulations and results on test formulations obtained by variation of the control formulations. In such test formulations it is the amount of the component marked with an asterisk in the above table which is correspondingly adjusted (i.e., so that the sum of all the components still totals 100 parts by weight). In making up the test formulations containing added material this is first dissolved in either the alcohol or methylene chloride (alcohol in the case of added hydroxypropylcellulose, or methylene chloride in the case of polyoxyethylene or acrylic elastomer) with low shear, high turbulence mixing conditions.

EXPERIMENT 1

The products employed in this experiment were:
1. Control Product I
2. Test Product 1A—as Control Product I but containing only 0.4% resin
3. Test Product IB—as Test Product IA but containing 0.05% of hydroxypropyl cellulose of molecular weight about $10^6$ (Klucel H)
4. Test Product IC—as Test Product IA but containing 0.04% of the hydroxypropyl cellulose in Test Product IB.

Products I, IA and IB were compared using the Switch Test Method and the following hold values were obtained:

| Product | Hold Value |
|---|---|
| Control Product | 8.3 |
| Test Product IA | 8.8 |
| Test Product IB | 6.5 |

Test Products IA and IC were compared separately with Control Product I by the Salon Test Method. The Control Product I gave better hold than Product IA at a significance level of less than 1%, whereas there was no difference in hold between Products I and IC.

EXPERIMENT 2

The products employed in this experiment were:
1. Control Product II

2. Test Product IIA—as Control Product II but containing 0.02% of hydroxypropylcellulose of molecular weight about $10^6$ (Klucel H)
3. Test Product IIB—as Control Product II but containing 3.00% of the resin
4. Test Product IIC—as Test Product IIA but containing 0.03% of the hydroxypropylcellulose
5. Test Product IID—as Control Product II but containing only 0.90% of the hairspray resin
6. Test Product IIE—as Test Product IID but containing 0.02% of the hydroxypropylcellulose in Product IIA.

Products II, IIA and IIB were compared by the Switch Test Method and the following hold values were obtained:

| Product | Hold Value |
| --- | --- |
| Control Product II | 4.2 |
| Test Product IIA | 2.9 |
| Test Product IIB | 3.5 |

Products II and IIC were compared with each other by the Salon Test Method. Product IIC gave better hold than Product II, the result being significant at less than the 1% level.

Products II, IID and IIE were used in a panel test in which each product was supplied to a separate group of about 130 women who used the respective product for two weeks. Statistical analysis of the evaluation of the products by the panelists showed that Product IIE gave better hold than Product IID at a significance level of 0.1% and Products II and IIE were not significantly different in holding power.

EXPERIMENT 3

The products employed in this experiment were:
1. Control Product III
2. Test Product IIIA—as Control Product III but containing 0.05% of hydroxypropylcellulose of molecular weight about $10^6$ (Klucel H)
3. Test Product IIIB—as Test Product IIIA but containing 0.15% of the hydroxypropylcellulose
4. Test Product IIIC—as Test Product IIIA but containing 0.10% of the hydroxypropylcellulose Products III, IIIA and IIIB were compared by the Switch Test Method and the following hold values were obtained:

| Product | Hold Value |
| --- | --- |
| Control Product III | 7.6 |
| Test Product IIIA | 5.1 |
| Test Product IIIB | 4.0 |

Products III and IIIC were compared by the Salon Test Method and Product IIIC was shown to produce a better hold than Product III, the result being significant at less than the 1% level.

EXPERIMENT 4

The products employed in this experiment were:
1. Control Product IV
2. Test Product IVA—as control product IV but containing only 0.75% of the hairspray resin and 0.04% of hydroxypropylcellulose of molecular weight about $10^6$ (Klucel H)

These products were compared using the Switch Test Method and the following hold values obtained:

| Product | Hold Value |
| --- | --- |
| Control Product IV | 6.2 |
| Test Product IVA | 5.3 |

The products were also compared with each other by the Salon Test Method and found not to differ in their holding power.

EXPERIMENT 5

The products employed in this experiment were:
1. Control Product V
2. Test Product VA—as control product V but containing only 0.70% of the hairspray resin
3. Test Product VB—as test product VA but containing 0.06% of hydroxypropylcellulose of molecular weight about $10^6$ (Klucel H).

These products were compared using the Switch Test Method and the following hold values were obtained:

| Product | Hold Value |
| --- | --- |
| Control Product V | 2.1 |
| Test Product VA | 5.3 |
| Test Product VB | 2.3 |

EXPERIMENT 6

The products employed in this experiment were:
1. Control Product VI
2. Test Product VIA—as control product VI but containing only 0.55% of the hairspray resin and 0.45% of a hydroxypropylcellulose having a molecular weight of about $1 \times 10^5$ (Klucel L) which is not a drag reducing agent.
3. Test Product VIB—as control product VI but containing only 0.55% of the hairspray resin and 0.07% of a hydroxypropylcellulose having a molecular weight of about $1 \times 10^6$ (Klucel H)
4. Test Product VIC—as control product VI but containing 0.07% of the hydroxypropylcellulose in test product VIB.

These products were compared using the Switch Test Method and the following hold values were obtained:

| Product | Hold Value |
| --- | --- |
| Control Product VI | 5.7 |
| Test Product VIA | 5.5 |
| Test Product VIB | 3.9 |
| Test Product VIC | 2.5 |

EXPERIMENT 7

The products used in this experiment were:
1. Control Product VII
2. Test Product VIIA—as control product VII but containing 0.02% of hydroxypropylcellulose of molecular weight about $1 \times 10^6$ (Klucel H)
3. Test Product VIIB—as test product VIIA but containing no hairspray resin
4. Test Product VIIC—as control product VII but containing no hairspray resin These products were compared using the Switch Test Method and the following hold values were obtained:

| Product | Hold Value |
| --- | --- |
| Control Product VII | 4.7 |
| Test Product VIIA | 2.2 |
| Test Product VIIB | 9.3 |
| Test Product VIIC | 9.7 |

EXPERIMENT 8

The products used in this experiment were:
1. Control Product VIII
2. Test Product VIIIA—as control product VIII but containing 0.005% of a polyoxyethylene having a molecular weight of about $6 \times 10^5$ (Polyox 205)
3. Test Product VIIIB—as test product VIIIA but containing 0.010% of the polyoxyethylene
4. Test Product VIIIC—as control product VIII but containing 0.001% of a polyoxyethylene having a molecular weight of about $4 \times 10^6$ (Polyox 301)
5. Test Product VIIID—as test product VIIIC but containing 0.004% of the polyoxyethylene
6. Test Product VIIIE—as control product VIII but containing 0.15% of a polyoxyethylene having a molecular weight of about $2 \times 10^5$ (Polyox 80).

The products were compared in three different tests by the Switch Test Method and the following hold values were obtained:

| Product | Hold Value | | |
| --- | --- | --- | --- |
| Control Product VIII | 8.6 | 9.1 | 8.8 |
| Test Product VIIIA | 6.1 | — | — |
| Test Product VIIIB | 5.2 | — | — |
| Test Product VIIIC | — | 6.8 | — |
| Test Product VIIID | — | — | 3.9 |
| Test Product VIIIE | — | — | 4.5 |

EXPERIMENT 9

The products used in this experiment were:
1. Control Product IX
2. Test Product IXA—as control product IX but containing 0.002% of a polyoxyethylene having a molecular weight of about $4 \times 10^6$ (Polyox 301)
3. Test Product IXB—as test product IXA but containing 0.004% of the polyoxyethylene The products were compared by the Switch Test Method and the following hold values were obtained:

| Product | Hold Value |
| --- | --- |
| Control Product IX | 6.8 |
| Test Product IXA | 3.6 |
| Test Product IXB | 3.2 |

EXPERIMENT 10

The products used in this experiment were:
1. Control product IX
2. Test Product IXC—as control product IX but containing 0.01% of a poly(ethyl acrylate)rubber of average Mooney viscosity 45 (Hycar 4021-45)
3. Test Product IXD—as test product IXC but containing 0.03% of the acrylic elastomer These products were compared using the Switch Test Method and the following hold values were obtained:

| Product | Hold Value |
| --- | --- |
| Control Product IX | 7.3 |
| Test Product IXC | 5.2 |
| Test Product IXD | 3.8 |

EXPERIMENT 11

The products used in this experiment were:
1. Control Product X
2. Test Product XA—as control product X but containing 0.02% of hydroxypropylcellulose of molecular weight about $1 \times 10^6$ (Klucel H)
3. Test Product XB—as control product X but containing only 1.00% of the hairspray resin
4. Test Product XC—as test product XB but containing 0.02% of the hydroxypropylcellulose in test product XA The products were compared by the Switch Test Method and the following hold values were obtained:

| Product | Hold Value |
| --- | --- |
| Control Product X | 5.5 |
| Test Product XA | 2.1 |
| Test Product XB | 6.3 |
| Test Product XC | 4.3 |

EXPERIMENT 12

The products used in this experiment were:
1. Control Product XI
2. Test Product XIA—as product XI but containing 0.05% hydroxypropylcellulose of molecular weight about $1 \times 10^6$ (Klucel H)
3. Test Product XIB—as product XIA but containing 0.15% of the hydroxypropylcellulose Products XIA and XIB were separately compared with control product XI by the Salon Test Method. Both of products XIA and XIB were found to give better hold than the control product XI. The result with product XIA was significant at the 1% level and with product XIB the result was significant at less than the 1% level.

EXPERIMENT 13

The products used in this experiment were:
1. Control Product XII
2. Test Product XIIA—as product XII but containing 0.00075% of a polyoxyethylene of molecular weight about $4 \times 10^6$ (Polyox 301)

The products were compared by the Switch Test Method and the following hold values were obtained:

| Product | Hold Value |
| --- | --- |
| Control Product XII | 4.4 |
| Test Product XIIA | 3.1 |

EXPERIMENT 14

The products used in this experiment were:
1. Control Product XIII

2. Test Product XIIIA—as product XIII but containing 0.10% of hydroxypropylcellulose having a molecular weight of about $1 \times 10^6$ (Klucel H)

The products were compared by the Switch Test Method and the following hold values were obtained:

| Product | Hold Value |
|---|---|
| Control Product XIII | 5.3 |
| Test Product XIIIA | 4.0 |

EXPERIMENT 15

The following hairspray products were made and packaged in containers fitted with a pump dispenser known as a CALMAR MISTETTE pump as described in Modern Packaging, October 1975, pages 15 to 20.

|  | Control Product XIV | Test Product XIVA |
|---|---|---|
| Hairspray Resin[1] | 4.00 | 4.00 |
| 2-Amino-2-methyl-1-propanol | 0.40 | 0.40 |
| Industrial methylated spirit | 95.60 | 95.57 |
| Hydroxypropylcellulose[2] | — | 0.03 |

[1] As in control product II
[2] Molecular weight about $1 \times 10^6$ (Klucel H)

These products were compared by the Switch Test Method and the following hold values obtained:

| Product | Hold Value |
|---|---|
| Control Product XIV | 4.4 |
| Test Product XIVA | 3.3 |

The above experiments demonstrate the very advantageous effect on the holding power of a hairspray that can be obtained by the inclusion of a minor amount of a drag reducing polymer in the hairspray. Many of the Experiments illustrate the benefit of the simple addition of the drag reducing polymer and in particular reference is made to the comparisons made by the Salon Test Method (between products IIC and II; products IIIC and III; and between both of products XIA and XIB and product XI) where the product containing the small amount of drag reducing agent in each case gave an improvement in hold which was better than the control product at a significance level of 1% or less. The Experiments also demonstrate that inclusion of a drag reducing agent enables the amount of the hairspray resin to be very substantially reduced without loss of holding power. This most surprising result is demonstrated by the comparisons conducted on products I (1.2% hairspray resin) and IC (0.4% hairspray resin); products II (1.8% hairspray resin) and IIE (0.90% hairspray resin); products IV (1.35% hairspray resin) and IVA (0.75% hairspray resin); products V (1.40% hairspray resin) and VB (0.70% hairspray resin); products VI (1.00% hairspray resin) and VIB (0.55% hairspray resin); and products X (1.50% hairspray resin) and XC (1.00% hairspray resin). The benefit in holding power arising from the inclusion of the drag reducing agent is manifestly far greater than could ever have been predicted and, indeed, the additions made of the drag reducing polymer are so small that no measureable hold benefit at all could reasonably have been expected.

The inclusion of a drag reducing agent in a hairspray to improve the hold also has the advantage that it reduces the respirable fraction of the spray. Experiments performed with various hairspray formulae indicated below demonstrate the reduction in respirable fraction.

EXPERIMENT 16

In this experiment test products XIA and XIB (see Experiment 12) were compared with the control product XI and the RF0 values of the test products XIA and XIB expressed as percentages of the RF0 value of the control product were 28% and 16%, respectively.

EXPERIMENT 17

In this experiment the products were:
1. Control Product VIII
2. Test Product VIIIF—as control product VIII but containing 0.05% of hydroxypropylcellulose of molecular weight about $1 \times 10^6$ (Klucel H)
3. Test Product VIIIG—as product VIIIF but containing 0.10% of the hydroxypropylcellulose
4. Test Product VIIIH—as product VIIIF but containing 0.15% of the hydroxypropylcellulose
5. Test Product VIIIJ—as product VIIIF but containing 0.20% of the hydroxypropylcellulose The RF0 and RF1 values for products VIII, F,G,H and J, expressed as a percentage of the corresponding RF0 and RF1 values for the control product VIII are indicated below.

| Product | RF0 value as % of control product | RF1 value as % of control product |
|---|---|---|
| Test Product VIIIF | 46 | 47 |
| Test Product VIIIG | 36 | 35 |
| Test Product VIIIH | 30 | 30 |
| Test Product VIIIJ | 25 | 26 |

EXPERIMENT 18

In this experiment the products used were control product II and test product IIC (see Experiment 2).

The test product IIC gave RF0 and RF1 values which were only 24% and 21%, respectively, of the corresponding values for the control product II.

EXPERIMENT 19

In this experiment the products used were control product XIII and test product XIIIA (see Experiment 14).

Test product XIIIA gave an RF0 value which was only 36% of the corresponding value for the control product XIII.

EXPERIMENT 20

In this experiment the products used were control product XIV and test product XIVA (see Experiment 15).

Test product XIVA gave an RF0 value which was only 34% of the corresponding value for the control product XIV.

EXPERIMENT 21

The following aerosol hairspray (control product XV) comprising carbon dioxide as propellant was formulated.

|  | % |
|---|---|
| Hairspray resin[1] | 2.85 |
| 2-Amino-2-methyl-1-propanol | 0.28 |
| Methylene chloride | 25.00 |
| Industrial methylated spirit | 65.11 |
| Lanolin derivative (Lanexol) | 0.10 |
| Bitrex solution[2] | 0.07 |
| Sucrose octa-acetate | 0.10 |
| Perfume | 0.20 |
| Carbon dioxide[3] | to 100.00 |

[1]As in control product II
[2]As in control product II
[3]Giving a gauge pressure of 6.3 kg/cm$^2$ at 25° C.

Test product XVA was formulated having the above composition except that it contained 0.01% of hydroxypropylcellulose of molecular weight about $1 \times 10^6$ (Klucel H) and the amount of the industrial methylated spirit correspondingly reduced.

The RF0 and RF1 values of test product XVA were 78% and 77%, respectively, of the corresponding values for the control product XV.

EXPERIMENT 22

The following aerosol hairspray (control product XVI) comprising a hydrocarbon as propellant was formulated.

|  | % |
|---|---|
| Hairspray resin[1] | 2.00 |
| 2-Amino-2-methyl-propanediol | 0.18 |
| Ethanol | 64.82 |
| Water | 16.00 |
| CAP 40[2] | 17.00 |

[1]As in control product II
[2]A commercial hydrocarbon blend consisting mainly of a mixture of propane and butanes having a vapour pressure of about 3.2 bars at 25° C.

Test product XVIA was also formulated having the above composition save that it contained 0.01% of hydroxypropylcellulose having a molecular weight of about $1 \times 10^6$ (Klucel H) and the amount of the ethanol correspondingly decreased.

The RF0 and RF1 values for the test product XVIA were 61% and 63%, respectively, of the corresponding values for the control product XVI.

EXPERIMENT 23

A hairspray composition (control product XVII) was prepared from the ingredients indicated below and packaged in an aerosol container.

|  | % |
|---|---|
| Hairspray resin[1] | 2.50 |
| 2-Amino-1-methyl-1-propanol | 0.25 |
| Ethanol | 47.25 |
| Water | 20.00 |
| Propellant 12 | 30.00 |

[1]As in control product II

Test products containing polyoxyethylene resins in an amount of 0.01% were prepared, the amount of water being reduced correspondingly.

RF0 and RF1 values obtained with the test products expressed as a percentage of the corresponding values obtained for the control product XV are indicated below.

| Test Product | MW of polyoxyethylene | RF0 value as % of Control | RF1 value as % of Control |
|---|---|---|---|
| XVIIA | $4 \times 10^6$ | 12 | 13 |
| XVIIB | $6 \times 10^5$ | 25 | 34 |

What is claimed is:

1. A hairspray product consisting of a hairspray composition within a container for spraying the composition onto the hair, wherein the hairspray composition consists essentially of
   (A) about 0.4% to about 7.5% by weight of a hairspray resin;
   (B) about 5% to about 99.5% by weight of a solvent for the hairspray resin;
   (C) a drag reducing agent, dissolved in said solvent, in an amount effective to enhance the holding power of the hairspray composition, the weight ratio of the hairspray resin to the drag reducing agent being about 10,000:1 to about 2:1 and the amount of the drag reducing agent being less than about 0.3% by weight of the hairspray composition, said drag reducing agent being a polymer soluble in said solvent and of such a high molecular weight that it has a drag reduction efficiency of at least 2%; and
   (D) 0% to about 90% by weight of a propellant.
2. A hairspray product as claimed in claim 1, wherein the drag reducing agent is a non-ionic polymer.
3. A hairspray product as claimed in claim 1, wherein the drag reducing agent has a drag reduction efficiency of at least 10%.
4. A hairspray product as claimed in claim 1, wherein the drag reducing agent is soluble in at least one of ethanol, methylene chloride and water.
5. A hairspray product as claimed in claim 2, wherein the drag reducing agent is a hydroxypropylcellulose having an average molecular weight of at least $2 \times 10^5$.
6. A hairspray product as claimed in claim 5, wherein the hydroxypropylcellulose has an average molecular weight of at least $5 \times 10^5$.
7. A hairspray product as claimed in claim 2, wherein the drag reducing agent is a polyoxyethylene having an average molecular weight of at least $2 \times 10^5$.
8. A hairspray product as claimed in claim 7, wherein the polyoxyethylene has an average molecular weight of at least $4 \times 10^5$.
9. A hairspray product as claimed in claim 2, wherein the drag reducing agent is a poly(ethyl acrylate) elastomer.
10. A hairspray product as claimed in claim 1, wherein the propellant is selected from the group consisting of liquefied hydrocarbon propellants, liquefied halogenated hydrocarbon propellants and mixtures thereof.
11. A hairspray product as claimed in claim 1, wherein the hairspray composition consists essentially of:
    (A) said hairspray resin in an amount of about 0.4 to about 7.5% by weight of the composition;
    (B) about 5% to about 99.5% by weight of said solvent for the hairspray resin selected from the group consisting of ethanol, isopropanol, methylene chloride, 2-methoxyethanol, 2-ethoxyethanol, mixtures thereof, and mixtures thereof with water;
    (C) said drag reducing agent soluble in the solvent for the hairspray resin in an amount effective to enhance the holding power of the hairspray composition, the weight ratio of the hairspray resin to the drag reducing agent being from about 10,000:1 to about 5:1 and the amount of the drag reducing agent being less than about 0.3% by weight of the hairspray composition; and (D) 0 to 90% by weight of said propellant for discharging the hairspray composition from the container.

12. A hairspray product as claimed in claim 11, wherein the propellant is a liquefied gaseous propellant selected from the group consisting of the liquefied hydrocarbon propellants, liquefied halogenated hydrocarbon propellants and mixtures thereof.

13. An improved hairspray product consisting of a hairspray composition within a container for spraying the composition onto the hair, said composition consisting essentially of:

(A) about 0.4% to about 7.5% by weight of a hairspray resin;

(B) about 5% to about 99.5% by weight of a solvent for the resin; and (C) 0% to about 90% by weight of a propellant, the improvement consisting in the inclusion in the hairspray composition, dissolved in said solvent, of a drag reducing agent in an amount effective to enhance the hair-holding power of the hairspray composition, the weight ratio of the hairspray resin to the drag reducing agent being from about 10,000:1 to about 2:1 and the amount of the drag reducing agent being less than about 0.3% by weight of the hairspray composition, said drag reducing agent being a polymer soluble in said solvent and of such a high molecular weight that it has a drag reduction efficiency of at least 2%.

* * * * *